United States Patent [19]

Kuypers et al.

[11] Patent Number: 4,780,285
[45] Date of Patent: Oct. 25, 1988

[54] DEVICE FOR THE CARRYING OUT OF AN IMMUNOCHEMICAL DETERMINATION

[75] Inventors: Leonardus P. C. Kuypers, Tc Teeffelen; Gerrit Wolters, El Oss, both of Netherlands

[73] Assignee: Akzo N.V., Arnhem, Netherlands

[21] Appl. No.: 893,511

[22] Filed: Aug. 5, 1986

[30] Foreign Application Priority Data

Aug. 19, 1985 [NL] Netherlands ................. 8502271

[51] Int. Cl.⁴ ................ G01N 33/50; G01N 33/54
[52] U.S. Cl. ................... 422/102; 422/58; 436/535; 436/809; 436/823
[58] Field of Search ........... 422/58, 102; 436/535, 436/809, 823

[56] References Cited

U.S. PATENT DOCUMENTS

| | | | |
|---|---|---|---|
| 3,655,838 | 4/1972 | Price et al. | 264/13 |
| 3,862,302 | 1/1975 | Price et al. | 424/12 |
| 4,004,979 | 1/1977 | Avrameas et al. | 436/823 X |
| 4,017,597 | 4/1977 | Reynolds | 436/808 X |
| 4,162,003 | 7/1979 | Bartos et al. | 436/809 X |
| 4,397,959 | 8/1983 | Hechemy | 422/58 X |
| 4,626,513 | 12/1986 | Burton et al. | 436/535 X |
| 4,654,299 | 3/1987 | Lentfer | 435/7 |

OTHER PUBLICATIONS

Buttner, J., et al., J. Clin. Chem. Clin. Biochem., vol. 18, 1980, pp. 78–88.

*Primary Examiner*—Barry S. Richman
*Assistant Examiner*—Lynn M. Kummert
*Attorney, Agent, or Firm*—William M. Blackstone

[57] ABSTRACT

Device for the carrying out of an immunochemical determination comprising at least one holder which is provided with an opening at the top and to the inside of which an immunochemically active substance has been applied. The device is closed at the top by a removable closure means and the holder contains at least a second immunochemically active substance which, in the absence of test medium, in the form in which the second immunochemically active substance is contained in the closed holder, during storage and transport under normal conditions exhibits no interaction with the inside of the holder and is inert with respect to the immunochemically active substance applied thereto. The holder contains a solid, more or less spherical, freeze-dried particle which contains the second immunochemically active substance.

9 Claims, No Drawings

DEVICE FOR THE CARRYING OUT OF AN IMMUNOCHEMICAL DETERMINATION

The invention relates to a device for the carrying out of an immunochemical determination comprising at least one holder which is provided with an opening at the top and to the inside of which an immunochemically active substance (IAS1) has been applied.

A device of this type is known in which the IAS1, inter alia, is applied to the inside of the holder in order to reduce the number of operations which must be performed to carry out the immunochemical determination. Reduction of the number of operations is of importance in two respects: in the first place for institutions which have to carry out large numbers of the same determination, and in the second place for the do-it-yourself determination where the number of errors which can be made will be smaller if the number of operations to be performed is smaller. Endeavours are therefore diligently being made to develop devices which meet the above-named need.

In order to carry out, for example, a so-called Sandwich determination, it is necessary in general to add, apart from the test medium, at least also in addition an exactly known quantity of a second immunochemically active substance to the holder. After incubation and rinsing of this holder the substance to be determined can then as a rule be determined quantitatively or qualitatively. The addition of this second immunochemically active substance in accurate quantities provides a source of error and, if large numbers are involved, is laborious. It would therefore be of advantage to provide a device, the holder(s) of which also contain(s) the said second immunochemically active substance so that the person who carries out the determination no longer has to add the said substance.

U.S. Pat. No. 4,017,597 provides a solution to this problem. The second immunochemically active substance is added to a holder, coated with the first immunochemically active substance, in dissolved form and subsequently the second immunochemically active substance is frozen to approximately $-78°$ C. within 5 to 15 seconds and lyophilized. Another method, introducing the second immunochemically active substance as a solid powder, is considered possible but not practical. Although the above reference presents a solution to the problem of avoiding the need of addition of the second immunochemically active substance by the person who is conducting an immunochemical determination, a number of drawbacks are introduced as well.

First of all, despite the short time, the second immunochemically active substance is present in dissolved form in the coated tube for some time. If the first immunochemically active substance is an antibody and the second immunochemically active substance is the corresponding antigen, some interaction will take place. Further some interaction between the wall and the second immunochemically active substance will take place.

Secondly, cooling of great numbers of tubes or microtiter plates to $-78°$ C. within 15 seconds requires technically sophisticated and costly measures Further, the lyophilisation of great numbers of tubes or microtiter plates requires very big and costly lyophilisation rooms.

The present invention provides a device, a which avoids the need to add the second immunochemically active substance for the person conducting the immunochemical determination and the drawbacks of the above reference, by applying a solid, more or less spherical, freeze-dried particle, which contains the second immunochemically active substance. Said particles is prepared before the second immunochemically active substance is contacted with the inside wall of the tube or with the first immunochemically active substance.

Accordingly, the present invention is concerned with a device for the carrying out of an immunochemical determination comprising at least one holder which is provided with an opening at the top and to the inside of which an immunochemically active substance has been applied and which is closed at the top by a removable closure means, the holder containing at least a second immunochemically active substance which, in the absence of test medium, in the form in which the said second immunochemically active substance is contained in the closed holder, during storage and transport under normal conditions exhibits no interaction with the inside of the holder and is inert with respect to the immunochemically active substance applied thereto, characterised in that the holder contains a solid, more or less spherical, freeze-dried particle which contains the second immunochemically active substance.

As already said the particle is prepared before the second immunochemically active substance (IAS2) is contacted with the inside wall of the tube or with the first immunochemically active substance (IAS 1). This avoids the drawbacks mentioned above. Further, the device according to the present invention exhibits an improved extent of significance, which means that the detection limit of the device according to the present invention is improved with respect to the device according to U.S. Pat. No. 4,017,597. Although this improvement is not fully understood until now, it is considered very surprising.

It has emerged that the selectivity, the sensitivity and the specificity of determinations carried out by means of the device according to the invention reveal the same quality even after long-term storage as a method of determination by means of a known device where IAS2 is added during the determination.

The device comprises at least one holder. If the device comprises one holder, the device may consist of a test tube, the inside of which is provided with IAS1 and which contains a second IAS which exhibits no interaction with the inside wall and is inert with respect to the IAS1 and the top of which is closed by means of a lid. Test tubes and lids of this type are known per set and may consist of glass or synthetic polymers such as, for example, polystyrene. The test tube is preferably transparent. Lid and test tube may consist of the same material, but this is by no means essential. The shape and dimensions of the test tube may vary within wide limits. The shape of the test tube may be rectangular, conical or hemispherical at the bottom, preferably the tube is hemispherical at the bottom. The height of the tube may vary, for example, from 1 cm to 10 cm and the inside diameter from 0.3 to 5 cm and preferably from 0.5 to 3 cm. The lid may be mounted on the test tube in a manner known per se, provided the method of mounting is such that the lid is removable and that the lid closes the test tube in an airtight manner.

The device may very appropriately also contain several holders, it being possible for the number to vary within wide limits, for example from 2 to 1000 and preferably from 10 to 500 and in particular from 25 to 200. The holders may very appropriately be mutually connected by means of the same material as the holders themselves consist of. As regards the material the same applies as has already been described above for a device with one holder. Here too the dimensiions of the holders may vary within wide limits. In general the dimensions of the said holders will be smaller than if the device comprises one holder. The height can vary from 0.2 to 4 cm and preferably from 0.3 to 2 cm and the inside diameter from 0.3 to 2 cm, preferably from 0.4 to 1.0 cm. A very appropriate device with several holders is a so-called microtiter plate in which each holder is sealed by a separate closure means. Preferably a microtitre plate is used which is provided with mutually connected closure means. An appropriate means for this purpose is a plate which is provided with studs which project 1 to 3 mm and close the holders in an airtight manner. In particular a plate provided with studs of silicone rubber may appropriately be used for this purpose.

The internal wall of the holder or holders is provided with an immunochemically active substance (IAS1) which is applied thereto in manners known per se, such as by means of covalent coupling or adsorption. This can be appropriately done by introducing an IAS1 solution or suspension into the holder(s) and after some time, for example 3–24 hours, removing the solution or suspension from the holder. As a result of adsorption the IAS1 will remain behind adhering to the inside wall of the holder(s). In general, not more than 80% of the inside wall surface of the holder(s) will be provided with IAS1 to prevent the IAS1 being dislodged from the inside wall of the holder(s) by the closure means being closed.

If the device comprises several holders, the inside wall of the holders may be provided with IAS1 and all the holders may contain IAS2; this is, however, not necessary. It may be of advantage that the device contains one or a few holders which lack IAS1 or IAS2 or IAS1 and IAS2 or a combination thereof in which blank determinations can be carried out. For calibrating determinations some holders may contain, in addition to the particle containing IAS2, a solid, more or less spherical freeze-dried particle containing the substance which is to be determined.

The IAS2 should be contained in the holders in a form such that no interaction takes place with either the inside of the holders or with the IAS1 during storage and transport under normal conditions. The IAS2 is treated for this purpose before being brought into contact with the inside wall of the holder and the IAS1. Further it is of importance for devices of this kind that accurately known quantities of immunochemically active substance are present. The particles which are contained in the holders of the device according to the present invention are formed by allowing a drop of an aqueous IAS2 solution or suspension, the drop having an accurately known and reproducible volume, preferably of 0.025–0.070 ml, to fall in freefall through a cold liquid immiscible with water which has a lower density than that of water, to collect the frozen pellets at the bottom surface of the cold liquid and to freeze-dry. In this way solid, stable, more or less spherical particles are obtained which contain an accurately known, reproducible quantity of IAS2, preferably with a diameter of approximately 3.6–5.2 mm. "More or less spherical" means in this respect that form which is obtained by allowing a drop of water to fall through a liquid which freezes the drop.

It is of advantage to add to the aqueous solution or suspension of IAS2 a substance which imparts firmness to the freeze-dried particles, i.e. a stiffener, for example sugars such as sucrose, mannose, lactose and mannitol and proteinaceous products such as serum protein, lactalbumin hydrolysate and casein hydrolysate. The corresponding particle will contain the stiffener.

As liquids which are immiscible with water a hydrocarbon or halogenated hydrocarbon or a mixture thereof may be used, such as hexane, chloroform, heptane, isooctane, toluene, hexane-chloroform mixtures and benzene-hexane mixtures or cryogenic liquids such as liquid nitrogen or liquid oxygen. At the bottom surface of the liquid column the temperature of the liquid which is not miscible with water is preferably below $-50°$ C.

In the form in which the IAS2 is contained in the sealed holder, the IAS2 should, in the absence of test medium, exhibit no interaction with the inside wall of the holder and be inert with respect to the IAS1 during storage and transport of the device under normal conditions. In this context "exhibit no interaction" and "inert" mean no binding or only binding, in any manner whatsoever, to the inside wall of the holder or the IAS1 to such an extent that the quality of determinations carried out with the device according to the invention experiences no appreciably adverse effect from it. "Normal conditions" means those conditions which are usual for storage and transport of comparable known devices. In general a temperature of $-25°$ C. to $+37°$ C. and preferably from $-20°$ C. to $20°$ C. at atmospheric pressure will be maintained during storage and transport.

In order to increase further the quality of the determinations performed with the device, the device is dried without sealing means and IAS2; then the freeze-dried, solid, more or less spherical particles which contain IAS2 are introduced into the holders preferably in a dry room and finally the holders are sealed in an airtight manner with the sealing means, also preferably in a dry room.

Often the test system will have to be buffered during a test. For this purpose the holder(s) of the device according to the invention can appropriately contain a freeze-dried, more or less spherical particle which contains buffer material and is prepared in the same way as the IAS2 particle. The greatest preference, however, is for a particle prepared starting from an aqueous IAS2 solution or suspension which contains an adequate amount of the desired buffer material. The freeze-dried, more or less spherical IAS2 particle then also contains buffer material.

The holder(s) of the device according to the invention may appropriately contain several immunochemically active substances (IAS3, IAS4 etc.), provided the said substances meet the criteria which IAS2 has to meet and provided the substances in the form in which they are introduced are also inert with respect to each other and the IAS2 under the circumstances already described. IAS3, IAS4 etc. are preferably treated in the same manner as the IAS2, freeze-dried, more or less spherical IAS3, IAS4 etc. particles then being obtained. A test method in which the device according to the invention with holders which contain an IAS2 and an IAS3 particle can appropriately be used is the inhibition test in which IAS3 contains a substance which is immunologically equivalent or immunologically complementary to the immunochemically active substance which it is desired to determine. In other test methods for which the device according to the invention can be used, such as the Sandwich test and the competitive test, a single IAS2 particle is sufficient.

With the device according to the invention, depending on the IAS1 and IAS2 (and possibly IAS3) and depending on the chosen test method, antibodies, antigens and haptens can be determined.

In the Sandwich test IAS1 and IAS2 are antibodies if an antigen has to be determined, and antigens or antiantibodies if an antibody has to be determined. IAS1 and IAS2 may be both polyclonal and monoclonal antibodies on the understanding that if IAS1 and IAS2 are monoclonal antibodies against the antigen to be determined, the IAS1-antibodies should often be directed against an antigen determinant other than the IAS2 antibodies. If the substance to be determined has two or more identical antigen determinants or if the substance to be determined, although itself not in the possession of two identical determinants, is present in the test medium in a cluster form such that the cluster has two or more identical antigen determinants, IAS1 and IAS2 may be monoclonal antibodies directed against the same antigen determinant.

In the competitive test the IAS2 is an antigen or hapten if the IAS1 is a monoclonal or polyclonal antibody, while the IAS2 is a monoclonal or polyclonal antibody if the IAS1 is an antigen or hapten.

If the IAS1 is a monoclonal or polyclonal antibody in the inhibition test, the IAS2 should also be a monoclonal or polyclonal antibody and the IAS3 an antigen, while the IAS2 should be an antigen or hapten and the IAS3 an antibody if the IAS1 is an antigen or hapten. Here too the above-mentioned preference applies if IAS1 and IAS2 are monoclonal antibodies.

To make detection possible the IAS2 should be provided with a labelling substance or after incubation with test medium and rinsing of the holder should be brought in contact with a substance which binds to IAS2 and which is provided with a labelling substance. Preferably the IAS2 itself is provided with a labelling substance. The labelling substance may be an isotope or an enzyme, dyestuff, fluorescent substance, metal-sol or dyestuff sol bonded to the IAS2.

An immunochemical determination method by means of the device according to the invention is generally carried out as follows. To the holder test liquid is added after the sealing means has been removed. Then incubation is carried out for some time. After the incubation the liquid is removed and the holder is rinsed after which the result of the test can be determined if the labelling substance is an isotope, dyestuff, fluorescent substance or metal particle. If the labelling substance is an enzyme substrate should also be added which is converted by the enzyme into a detectable substance.

With the device according to the invention immunochemical determinations may be carried out which, as regards specificity, sensitivity and selectivity are not second to determinations carried out with devices to which IAS2 and possibly IAS3 are added during or shortly before the determination even if the device according to the invention has been stored for months. The invention is explained in more detail by reference to the following examples.

EXAMPLE 1

Of four polystyrene microtitre plates which contain 8 rows of 12 conically cylindrical holders (height 10 mm, upper diameter 6.5 mm, lower diameter 6 mm) with a flat bottom, a number of holders were filled with 0.135 ml of an aqueous solution which contained IAS1. After 16 hours the liquid was removed and the microtitre plates were dried for 24 hours at 20° C. in air with a relative humidity of <20%. Microtitre plates 1 and 2 were immediately used for a number of determinations in which, after the test medium had been added to the holders, to the holders of microtitre plate 1 a drop of an aqueous IAS2 solution was added and to the holders of microtitre plate 2 as a particle containing IAS2 prepared as described below starting from a drop having the same volume and the same concentration of IAS2 as the drop which was added to the holders of microtitre plate 1 was added. To the holders of microtitre plates 3 and 4 were added particles containing IAS2 in a dry room, also prepared as described below starting from a drop with the same volume and the same concentration of IAS2 as the drop which was added to the holders of microtitre plate 1. To some holders particles containing IAS3 were also added. Microtitre plates 3 and 4 were then sealed in the same dry room with a sealing means provided with studs, projecting 2.5 mm, of silicone rubber which closed the holders of the microtitre plates in an airtight manner, and stored for 1 week or 3 months respectively at 18° C. and atmospheric pressure.

From a solution which contained an accurately known quantity of IAS2, buffer and sucrose, 0.05 ml drops were passed by means of a drop pipette in free fall through a Dewar flask filled with 80 cm of liquid nitrogen. At the bottom the solid, more or less spherical particles were gathered and freeze-dried. These particles were used in the holders of the microtitre plates 2, 3 and 4. Particles which contained IAS3 were prepared in the same manner.

The determinations were carried out as follows. After the test medium, which contained an accurately known quantity of the substance to be determined, had been added, incubation was carried out for some time at 37° C.; this was followed by rinsing with buffer and detection. If an enzyme (peroxidase) was used as labelling substance, a further incubation step using a peroxide-containing substrate was carried out before the detection. Detection took place in the various examples in a colorimetric manner.

Examples 1, 4, 7, 10, in which HBsAg was determined, were carried out in an identical manner on the understanding that in Example 1 a drop of liquid containing IAS2 and in Examples 4, 7 and 10 particles containing IAS2 were used, the time after which the test was carried out after the particles had been added to the holders varying. The same applies to Example Groups 2, 5, 8, 11 and 3, 6, 9, 12 in which HCG and testosterone were determined respectively. Each of the examples was carried out 10 times; the quantity found, which is shown in the last column of Table 1, is the average of these 10 determinations.

As should be evident from the results, the quality of the determinations performed with the device according to the invention is the same as that of determinations performed with known devices. The device according to the invention has in addition the advantage that the person who has to carry out the determination does not have to add an accurately known quantity of IAS2 to the holder(s).

TABLE 1

| Example | Micro-titre plate | IAS1 | IAS2 | Labelling substance | Type of test | Test Medium | IAS3 | Incubation time | Quantity found |
|---|---|---|---|---|---|---|---|---|---|
| 1 | 1 | M anti-HBs | anti-HBs | enzyme | Sandwich | 0.1 ml serum | N.A. | 1 h. | 1.0 ng/ml |
| 2 | 1 | HCG | anti-HCG | gold sol | competitive | 0.1 ml urine | N.A. | 1 h. | 1010 IU/l |
| 3 | 1 | anti-T | anti-T | dyestuff | inhibition | 0.1 ml PBS | T-BSA (added in drop form) | 2 h. | 250 ng/ml |
| 4 | 2 | M anti-HBs | anti-HBs | enzyme | Sandwich | 0.1 ml serum | N.A. | 1 h. | 1.0 ng/ml |
| 5 | 2 | HCG | anti-HCG | gold sol | competitive | 0.1 ml urine | N.A. | 1 h. | 1012 IU/l |
| 6 | 2 | anti-T | anti-T | dyestuff | inhibition | 0.1 ml PBS | T-BSA | 2 h. | 252 ng/ml |
| 7 | 3 | M anti-HBs | anti-HBs | enzyme | Sandwich | 0.1 ml serum | N.A. | 1 h. | 1.0 ng/ml |
| 8 | 3 | HCG | anti-HCG | gold sol | competitive | 0.1 ml urine | N.A. | 1 h. | 980 IU/l |
| 9 | 3 | anti-T | anti-T | dyestuff | inhibition | 0.1 ml PBS | T-BSA | 2 h. | 245 ng/ml |
| 10 | 4 | M anti-HBs | anti-HBs | enzyme | Sandwich | 0.1 ml serum | N.A. | 1 h. | 1.0 ng/ml |
| 11 | 4 | HCG | anti-HCG | gold sol | competitive | 0.1 ml urine | N.A. | 1 h. | 1013 IU/l |
| 12 | 4 | anti-T | anti-T | dyestuff | inhibition | 0.1 ml PBS | T-BSA | 2 h. | 257 ng/ml |

PBS = phosphate-buffered physiological salt solution
HBsAg = hepatitis B surface antigen
anti-HBs = antibody (sheep) against HBsAg
M anti-HBs = monoclonal antibody (mouse) against HBsAg
HCG = human chorion gonadotrophin
anti-HCG = antibody (rabbit) against HCG
T = testosteron
anti-T = antibody (rabbit) against T
T-BSA = several T molecules coupled to a bovine serum albumin molecule
N.A. = not applicable

EXAMPLE 2

Of two microtiter plates 23 holders were coated with M-anti-HBsAg as in Example 1. Subsequently, 0.050 ml of an aqueous solution which contained anti-HBsAg, labeled with a peroxidase, was added to the coated holders of one microtiter plate at 0° C. The solution was frozen within 15 seconds to −78° C. and then the microtiter plate was freeze-dried for 16 hours. To the coated holders of the other microtiter plate a particle containing anti-HBsAg, labeled with a peroxidase, and prepared as in Example 1 was added. Thereafter enzyme immuno-assays were performed in both microtiter plates with 19 different human sera which did not contain HBsAg and two times with sera containing 0.1 U/ml and 1.0 U/ml of HBsAg respectively. The assay and the detection was carried out as in Example 1.

The extent of significance was calculated from the formula $$X - Y/Z$$

where X = the average of the values measured for the sera containing 0.1 or 1.0 U HBsAg/ml, Y = the average of the values measured for the sera which did not contain HBsAg and Z = the standard deviation of Y.

In Table 2 the results are given, which clearly show that the detection limit is lower for the device according to the present invention with respect to the detection limit for the device according to U.S. Pat. No. 4,017,597 (the higher the extent of significance the lower the detection limit).

TABLE 2

|  | 0.1 U HBsAg/ml | 1.0 U HBsAg/ml |
|---|---|---|
| invention | 8 | 88 |
| U.S. Pat. No. 4,017,597 | 3 | 41 |

U/ml are the units of HBsAg as defined by Paul Ehrlich Institute (Frankfurt, FRG) per ml.

We claim:

1. Device for the carrying out of an immunochemical determination comprising at least one sealable container means having an interior cavity capable of containing a liquid sample, said container means having a top portion and a bottom portion with an opening in the top portion thereof, the opening being closed by a removable closure means that permits the introduction of a liquid sample, said container means having a first immunochemically active substance coated onto at least a portion of a surface of the interior cavity, said container means also containing within the interior cavity at least one freeze-dried particle comprising a predetermined amount of at least one additional immunochemically active substance that, in the absence of test medium, has no chemical or physical interaction with said first immunochemically active substance, the container means or the closure means.

2. Device according to claim 1, wherein each freeze-dried particle comprises a stiffener.

3. Device according to claim 1, wherein the device comprises at least one container means each having only one, substantially spherical, freeze-dried particle in the interior cavity thereof.

4. Device according to claim 1, wherein each freeze-dried particle comprises buffer material.

5. Device according to claim 4, wherein each freeze-dried particle comprises a stiffener.

6. Device according to claim 1, wherein the device comprises 2–1000 container means.

7. Device according to claim 6, wherein the closure means comprises a plate having protrusions that individually seal the openings in the container means.

8. Device according to claim 6, wherein the device comprises a microtitre plate.

9. Device according to claim 8, wherein the closure means comprises a plate having protrusions that individually extend into and seal the openings in the microtitre plate.

* * * * *